Sept. 3, 1974 L. H. SHOESMITH Plant Pat. 3,609
CHRYSANTHEMUM (RED BONANZA)
Filed May 3, 1973
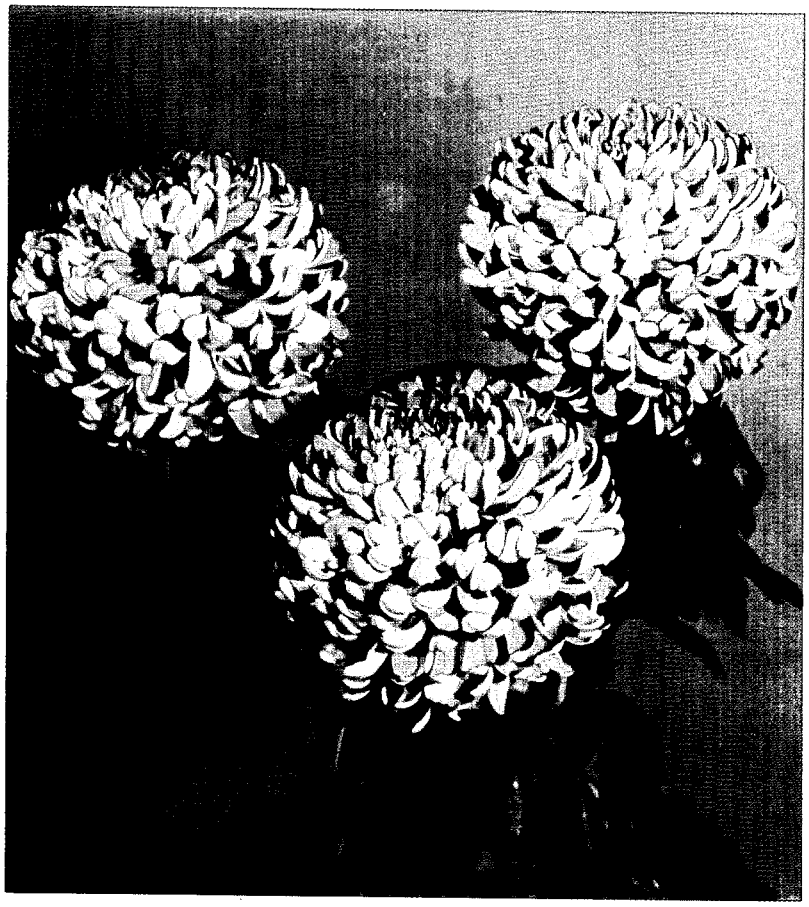
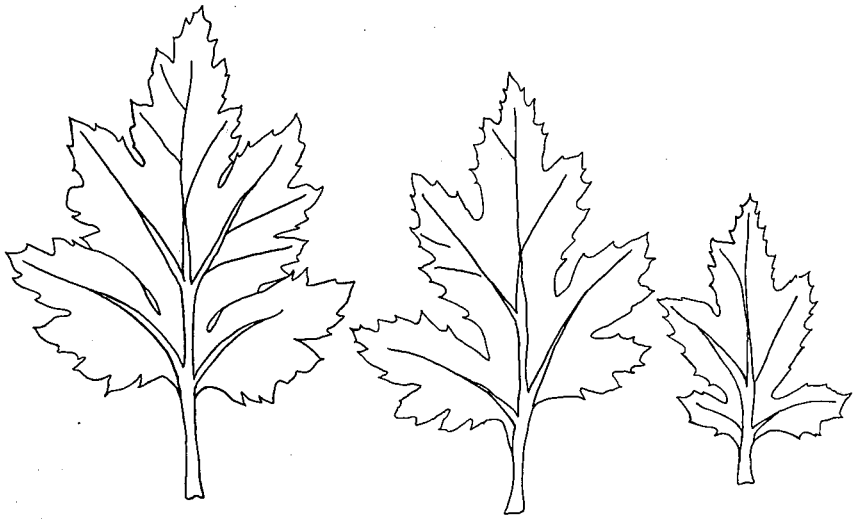

United States Patent Office

Plant Pat. 3,609
Patented Sept. 3, 1974

3,609

CHRYSANTHEMUM (RED BONANZA)

Leonard H. Shoesmith, Westfield, Woking, Surrey, England, assignor to Pan-American Plant Company, West Chicago, Ill.

Filed May 3, 1973, Ser. No. 356,921
Int. Cl. A01h *5/00*
U.S. Cl. Plt.—82 1 Claim

ABSTRACT OF THE DISCLOSURE

A new variety of chrysanthemum plant of the standard incurved type, suitable for glass house culture, particularly distinguished by its very large globular head of many florets which have a Cardinal Red inside surface color and a Mimosa Yellow reverse side or outer surface color, providing a bright firey appearance for the blossom.

Background of the New Plant

This new variety of chrysanthemum originated as a seedling of unknown parentage found by me in November 1968 among a stock of plants of mixed and unknown breeding, grown in greenhouse at West Chicago, Ill., and maintained in connection with an extensive breeding program carried on by me and under my direction with the objective of producing improved varies suitable for the cut flower and potted plant markets. This new plant was selected for propagation and test because of the unusual coloring and large size of its bloom, and asexual propagation by cuttings, under my direction, during more than four years of programmed testing at West Chicago, Ill., has proved this new plant to have its distinctive characteristics firmly fixed and to hold true from generation to generation. Present propagation of this new chrysanthemum variety is now being done in a commercial scale, by vegetative cuttings, at Cortez, Fla. as well as at West Chicago, Ill.

Description of the Drawing

My new variety of chrysanthemum is illustrated by the accompanying photographic drawing which shows the flower form and color characteristics as nearly true as it reasonably possible to obtain by conventional photographic procedures and which shows, by pen and ink drawing, the distinctive configuration of its leaves taken at several stages of maturity.

Description of the New Plant

The following is a detailed description of my new variety of chrysanthemum plant with color designations according to the Horticultural Color Chart (HCC) created by Robert F. Wilson and issued by The British Colour Council in collaboration with The Royal Horticultural Society of London, England.

THE PLANT

Origin: Seedling.
Parentage: Unknown, found among random pollinated greenhouse plants.
Classification:
- Botanic—Chrysanthemum morifolium.
- Commercial—Greenhouse pot plant.

Form: Perennial herbaceous bush.
Height: 2 to 4 feet.
Growth: Terminal. Vigorous and upright with good strength and normal branching.
Foliage: Moderate in quantity—about 30 leaves on 3 feet of stem.
- *Leaf Size.*—Average or middle size leaf—5 inches long x 4 inches wide, some larger, some smaller.
- *Leaf shape.*—Lanceolate and cleft, somewhat serrated.
- *Surface Texture.*—Glaucescent.
- *Venation.*—Pinnately.
- *Color.*—Upper Side—Ivy Green 0001060/3. Under Side—Spinach Green 0960/3.
- *Petioles.*—1½ inches long.

THE BUD

Form: Globular.
Size: 1¼ to 1½ inches in diameter and ½ inch in depth, just before florets begin to unfurl.
Opening Rate: Slow. Phyllaries begin to divide about two weeks from the time the bud becomes visible. Flowering occurs about four weeks later.
Color: When phyllaries first divide—Ruby Red 827/1. When florets begin to unfurl—Ruby Red 827/1 streaked with Mimosa Yellow 602/2.
Phyllaries: The outside of the receptacle bears many involucral bracts or phyllaries that are distinct. The calyx is represented by tiny bristles arising from the top of the ovary, or it may be absent.
Form: Spear-shaped and stand up.
Surface Texture: Canescent.
Color: Inside—Spinach Green 0960/2. Outside—Spinach Green 0960/2.
Peduncle: Color—Spinach Green 0960/2.

THE FLOWER

Response: 9 weeks. This plant can be flowered the year around with photoperiod control.
Natural Season Flowering: About Nov. 1.
Recommended Flowering: Late Spring, Summer, early Fall.
Blooms:
- *Flower Type.*—Incurve.
- *Size.*—Very large. Diameter—6 inches; Depth—4 inches.
- *Shape.*—Flat and round when bloom first opens. Becomes more globular as bloom matures.
- *Borne.*—A single head of many florets on a receptacle.
- *Florets.*—Form—Linear with obtuse apex. Color: Incurved surface—Cardinal Red 822/1 with undertone of Mimosa Yellow 602/2 and Canary Yellow 2/1 at base end; outer or reverse side—Mimosa Yellow 602/2 with Cardinal Red 822/1 showing through. Texture: Firm. Appearance: Velvety, Discoloration: Slight fading after full bloom.
- *Peduncle.*—2 to 2½ inches long, sturdy and upright. Color: Spinach Green 0960/2.

Persistence: Florets hang on and dry.
Effect of Weather: None.
Fragrance: None.
Lasting Quality: On plant—21 days. As cut flower—14 days.

REPRODUCTIVE ORGANS

Stamens: This plant has no stamens or pollen.
Pistils: One per floret. Style: About ¼ inch long.
*Stigmas.*—Color—Yellow.
Ovaries: Inferior and bicarpellate.

This plant most resembles Blaze (unpatented). When compared with Blaze, however, this plant has a larger bloom, is of a deeper red coloring and has many more florets. It is taller than Blaze and more vigorous in its growth habit. The form tends to be reflexed under low light intensities and is therefore most suitable for Spring, Summer and Fall flowering.

I Claim:

1. A new and distinct variety of chrysanthemum plant, substantially as herein shown and described, characterized by the very large size of its standard incurved type blooms which have many bi-colored florets showing a deep red on the incurved surfaces and bright yellow on the reverse sides, and by its tall and vigorous growth habit.

No references cited.

ROBERT E. BAGWILL, Primary Examiner